United States Patent [19]

Suga

[11] 3,998,551
[45] Dec. 21, 1976

[54] DEVICE FOR MEASURING STIMULUS VALUES OF THE COLOR OF A LIQUID

[76] Inventor: Shigeru Suga, Yoyogi 5-20=2, Shibuya, Tokyo, Japan

[22] Filed: Nov. 20, 1975

[21] Appl. No.: 633,908

[52] U.S. Cl. .............................. 356/73; 250/226; 250/228; 356/176; 356/178; 356/236
[51] Int. Cl.² ................... G01N 21/00; G01J 3/46
[58] Field of Search ............ 356/73, 176, 177, 178, 356/184, 236; 250/573, 574, 575, 226, 228

[56] References Cited
OTHER PUBLICATIONS

Trial Manufacture of Photoelectric Colorimeter using Optical Fibers; Ishikawa et al.; Bull. Tokyo Dent. Coll. vol 10, No. 4, pp. 191–197; Nov. 1969.

*Primary Examiner*—Vincent P. McGraw
*Attorney, Agent, or Firm*—Wenderoth, Lind & Ponack

[57] ABSTRACT

A device for measuring three stimulus values of the color of a liquid as a way of determining the color of the liquid. The device has an optical part having a source of light, an integrating ball having an inlet for light and three light receiving elements therein, and a light path switching device at the inlet. An immersible detector has a reflected light detector and a transmitted light detector as a part thereof, the reflected light detector having an opening therein and a flat transparent element covering the opening. The transmitted light detector is spaced from and aligned with the opening in the reflected light detector. A reflected light receiver in the reflected light detector is positioned to receive light reflected from the transparent element at an angle of 45° thereto. Optical fibers are connected between the source of light and the reflected light detector for directing light into the reflected light detector perpendicularly to the transparent element and between the reflected light receiver and the light path switching device and between the transmitted light detector and the light path switching device, respectively. A measuring device is electrically coupled to the light receiving elements in the integrating ball for indicating the amount of light received thereby. When the immersible detector is immersed in a liquid, the color of which is to be determined, the liquid fills the space between the reflected light detector and the transmitted light detector, and the transmitted light and reflected light are conducted to the light path switching device, and one type of light is first admitted to the integrating ball and the three stimulus values of the one type of light are measured by the measuring means, and then the light path switching device is actuated to admit the other type of light and the three stimulus values of the other type of light are measured.

2 Claims, 2 Drawing Figures

FIG.2

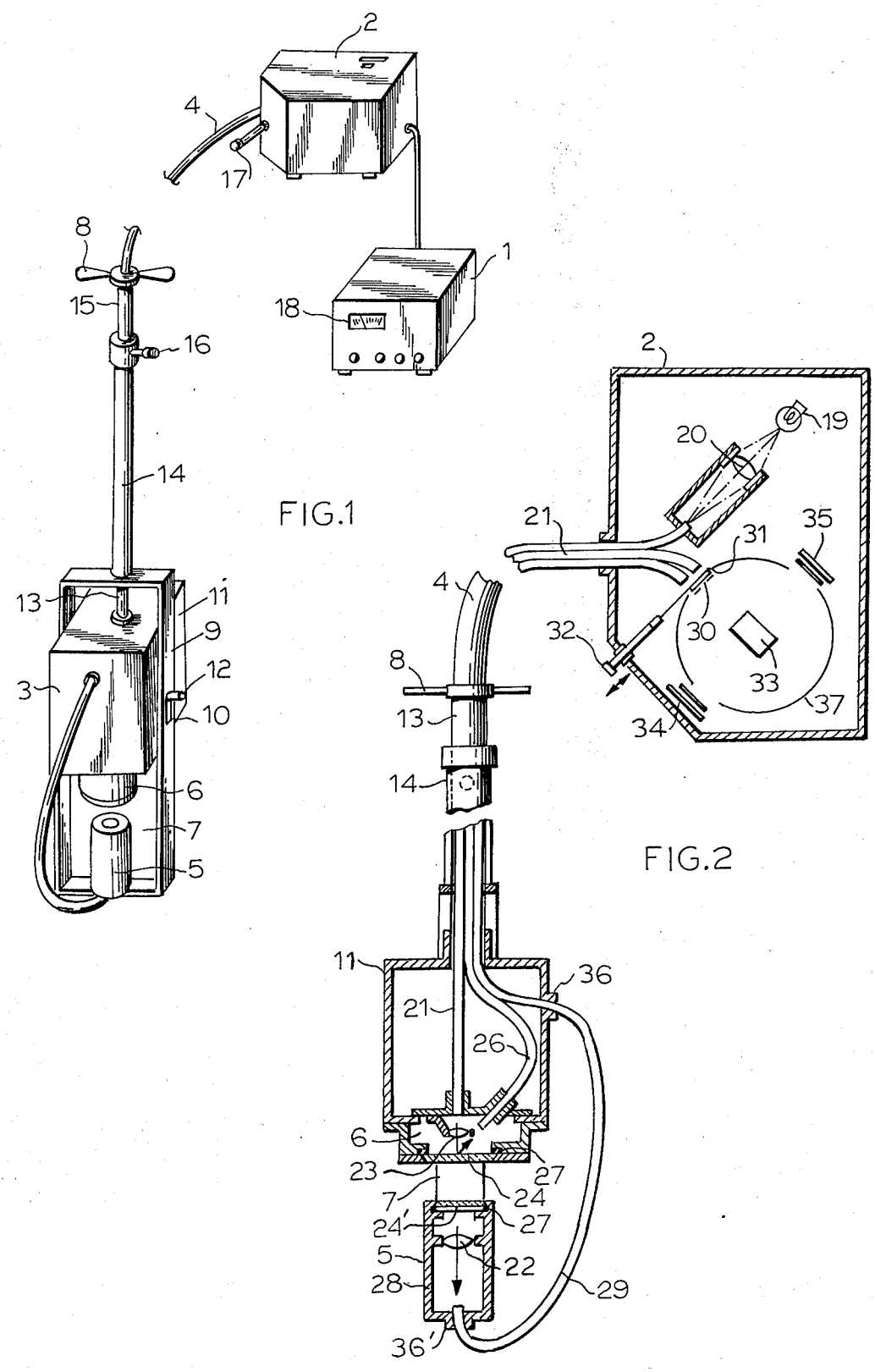

DEVICE FOR MEASURING STIMULUS VALUES OF THE COLOR OF A LIQUID

The present invention relates to a device for measuring three stimulus values as a way of determining the color of transmitted light and reflected light for foods and other colored liquids such as paints, juice, etc.

BACKGROUND OF THE INVENTION AND PRIOR ART

Heretofore, determination of the color of liquids has consisted of placing a specimen into a container which is attached to an optical system in an instrument such as a spectrometer or other color determining instrument, whereby only the color of the transmitted light is measured by the particular method of color determination.

However, in actual practice, the colors in both the transmitted light and reflected light for a liquid stimulate the visual nerve. Therefore, it is necessary to determine the color of both types of light simultaneously to evaluate the color of the liquid.

There has been, thus far, no instrument that can determine the color of the aforesaid two types of light. Although a turbidity-measuring instrument has heretofore been available, it is designed to measure the degree of light scattering caused by the particles in the liquid, and it has not been helpful in the evaluation of color.

OBJECT AND BRIEF DESCRIPTION OF THE INVENTION

It is an object of the present invention to provide a device for measuring three stimulus values as a way of determining the color of a liquid which overcomes the drawbacks of the prior art devices.

According to the device of the present inventon, means are provided to measure the optical conditions specified under the Japanese Industrial Standards, i.e. three stimulus values X, Y and Z of 0° incident light which is reflected at 45° and of transmitted light which is incident vertically to the surface of the liquid without requiring the operation of sampling.

BRIEF DESCRIPTION OF THE DRAWINGS

The invention will now be described in greater detail in connection with the accompanying drawings, in which:

FIG. 1 is a diagrammatic view of the general setup of the device for determining color according to the present invention; and FIG. 2 is a diagrammatic view similar to FIG. 1, partly in section, showing the internal structure of the detector part and the optical part of the device of FIG. 1.

FIG. 1 shows the setup of the device for determining the color of liquid according to the present invention. A measuring part 1 is electrically connected to an optical part 2 which in turn is connected to an immersible detector part 3 by an optical fiber means 4. The immersible detector part 3 has a transmitted light detector part 5 and a reflected light detector part 6 and a space 7 between said transmitted light detector part 5 and reflected light detector part 6 in which liquid, the color of which is to be determined, is present when the detector part 3 is immersed therein. A handle 8 is provided from which the detector part 3 is suspended from immersion in the liquid, the color of which is to be determined. The detector part 3 is mounted on a frame 9 which is suspended by pipe 14 and tube 13 from handle 8, and which has long holes 10 on both sides thereof in which guides 12 on the detector casing 11 can slide up and down. Detector part 5 is fixed on the bottom of frame 9.

The tube 13 contains the optical fiber 4 and extends through the pipe 14, and the lower end of the tube 13 is fastened to the casing 11, and the upper end has the handle 8 thereon. The numeral 15 designates a graduation on tube 13 for showing the level of casing 11 in frame 9, and hence the thickness of the liquid in space 7. On the pipe 14 connected to the frame 9 is a set screw 16 which holds the tube 13 in pipe 14. By loosening the screw 16, the casing 11 is freed for movement up and down on frame 9, so that the liquid layer can be set to a thickness suitable for the device to perform the necessary measurements to determine the color of the liquid in the space 7. For example, liquids of relatively faint colors may have a thickness of 10mm, and liquids having dark colors, such as soy-bean sauce, may have a thickness of 1mm. The numeral 17 is a lever for switching the light delivered to the optical part 2 from transmitted light to reflected light. The numeral 18 designates an indicator instrument or a digital voltmeter.

The internal construction of the detector part and the optical part is shown in FIG. 2.

The light from an incandescent lamp 19 is led through a lens 20 to an optical fiber 21. The other end of the fiber 21 extends through the casing 11 and opens into detector 6 to irradiate a liquid in the space 7 through a lens 23 and a glass plate 24. Of the light reflected by the liquid against the surface of the glass, the light reflected at an angle of 45° with respect to the source of light is led to the end of an optical fiber 26 in detector 6, which optical fiber 26 in turn extends back through the optical fiber means 4 to a lightpath switching means 30 provided at the inlet 31 of an optical integrating ball 37 within the optical part 2, the interior of which ball is white. This reflected light is dispersed in the ball 37 and received by light-receiving elements 33, 34 and 35 corresponding to the three stimulus values and made up of a filter, photoelectric cells, etc. in the integrating ball to measure the three stimulus values. The glass 24 is hermetically sealed in the opening of the detector 6 by a packing 27.

The transmitted light detector part 5, like the reflected light detector 6, has a glass plate 24' and a packing 27' hermetically sealing the glass in the casing 28 thereof. Light transmitted through the liquid in space 7 is led through a lens 22 to an optical fiber 29 in detector 5, which optical fiber 21 extends back through the optical fiber means 4 to the integrating ball 37, and, depending on the position of the light-path switching device 32, is received by the light-receiving elements 33, 34 and 35.

Seals 36 and 36' are provided around the optical fibers 26 and 29 where they extend out through the detector casings, which seals are made of an adhesive agent or a sealing material, so that no liquid can enter the casings when the detector part is immersed in the liquid, the color of which is to be determined.

The measuring part 1 has amplifier means and a constant voltage power supply for the source of light, and the photoelectric currents from the light-receiving elements are amplified indicated in terms of X, Y and Z values by means of a digial voltmeter 18 which can be switched to indicate the different X, Y and Z values. Alternatively, the measuring part 1 can have three voltmeters, one for each stimulus value.

To determine the color of the reflected light, the operating procedure for the device of the present invention consists of first placing a standard plate, the color of which is known, on the surface of the glass plate 24 before immersing the detecting part 3 into the liquid which is to be tested, and then, with the light path switching device 32 appropriately positioned, adjusting the resistance of the circuit so that the indication of the instrument will have a value corresponding to said known color.

To determine the color of the transmitted light, the operation consists of first setting the position of the casing 11 so that the thickness of the liquid layer in space 7 is, for example, 1mm without using a standard color plate, and then, with the light path switching device 32 switched over, adjusting the circuit for the transmitted light so that the Y value will be 100.0, the X value will be 98.04 and the Z value will be 118.10.

The thickness of the liquid layer in space 7 is then increased to 2, 3, 4 ... m/m by moving casing 11, and the relation of the Y values with respect to the various distances is determined.

Determination of the color of a specimen is then carried out by immersing the detecting part 3 therein so that the specimen liquid will sufficiently fill the space 7. Then with the light path, switching device 32 appropriately positioned, values for the transmitted light are measured for every 1 mm in the thickness of the layer in space 7. In this case, when the indicated value exceeds the full scale, the distance should be increased. On the contrary, when the indicated value is too small, the distance should be reduced to take measurements at an appropriate position. For example, if the measured values are X=28.4, Y=16.7 and Z=17.58 when the thickness is 3mm, true values can be found from a proportional relation between 1mm and 3mm.

The values for the reflected light can be measured by switching the light-path switching device 32 to admit reflected light from optical fiber 26, whereby X, Y and Z values are measured by the measuring part 1 based on the photoelectric current from the light-receiving elements 33, 34 and 35.

As indicated in the foregoing, with regard to determining the color of transmitted light, a thin liquid layer is used in the case of a dark liquid color, and a thick liquid layer is used in the case of a light liquid color. Therefore, any reflected light directed toward the transmitted light detector is always absorbed by the liquid layer and can be neglected.

As described above, with the device for determining color according to the present invention, it is possible to measure easily the three stimulating values of color for the transmitted light and for the reflected light without sampling the specimen liquid, because the detector part 3 is simply immersed in the specimen liquid.

What is claimed is:
1. A device for measuring three stimulus values of the color of a liquid as a way of determining the color of the liquid, comprising:
   an optical part having a source of light, an integrating ball having an inlet for light and three light receiving elements therein, and a light path switching device at said inlet;
   an immersible detector having a reflected light detector and a transmitted light detector as a part thereof, said reflected light detector having an opening therein and a flat transparent element covering said opening in liquid tight relationship therewith, said transmitted light detector being spaced from and aligned with said opening in said reflected light detector, a reflected light receiver in said reflected light detector positioned to receive light reflected from said transparent element at an angle of 45° thereto;
   light conducting means coupled between said source of light and said reflected light detector for directing light into said reflected light detector in alignment with said opening and perpendicularly to said transparent element, and further light conducting means coupled between the reflected light receiver and the light path switching device and between the transmitted light detector and the light path switching device, respectively; and
   a measuring means electrically coupled to said light receiving elements in said integrating ball for indicating the amount of light received thereby;
   whereby when the immersible detector is immersed in a liquid the color of which is to be determined, the liquid fills the space between the reflected light detector and the transmitted light detector, and the transmitted light and reflected light are conducted to the light path switching device, and one type of light is first admitted to the integrating ball and the three stimulus values of the one type of light are measured by the measuring means, and then the light path switching device is actuated to admit the other type of light and the three stimulus values of the other type of light are measured.
2. A device as claimed in claim 1 in which said light conducting means are optical fibers in liquid tight sealing engagement with said immersible detector.

* * * * *